United States Patent [19]

Ishimaru et al.

[11] 4,036,833

[45] July 19, 1977

[54] 7-[(5'-N-METHYLTHIOACETAMIDO)-ADIPOAMIDO] CEPHALOSPORIN DERIVATIVES

[76] Inventors: Toshiyasu Ishimaru, D-14, 2-7, Momoyamadai, Suita; Mariko Kawabata, 9-4, Tachibanacho-1 chome, Toyonaka, both of Japan

[21] Appl. No.: 580,965

[22] Filed: May 27, 1975

[30] Foreign Application Priority Data

May 28, 1974 Japan .................................. 49-61296
July 3, 1974 Japan .................................. 49-76771

[51] Int. Cl.² ........................................... C07D 501/36
[52] U.S. Cl. .................................. 260/243 C; 424/246
[58] Field of Search .................................. 260/243 C

[56] References Cited

U.S. PATENT DOCUMENTS

| 3,864,340 | 2/1975 | Ishimaru et al. | 260/243 C |
| 3,865,819 | 2/1975 | De Marinis et al. | 260/243 C |
| 3,910,900 | 10/1975 | Naito et al. | 260/243 C |
| 3,923,795 | 12/1975 | Spry | 260/243 C |

*Primary Examiner*—Nicholas S. Rizzo
*Assistant Examiner*—David E. Wheeler
*Attorney, Agent, or Firm*—Hubbell, Cohen, Steifel & Gross

[57] ABSTRACT

New N-substituted thio (or sulfinyl) aliphatic acylcephalosporin C and their derivatives at the 3rd position have been prepared. The compounds are useful as intermediates for recovering cephalosporin C and deacetoxycephalosporin C from their fermentation broth and also for preparing 7-aminocephalosporanic acid and its derivatives at the 3rd position.

5 Claims, No Drawings

7-[(5'-N-METHYLTHIOACETAMIDO)-ADIPOAMIDO] CEPHALOSPORIN DERIVATIVES

This invention relates to new cephalosporin derivatives and a process for the preparation of the same.

More particularly, the invention provides new cephalosporin derivatives of the general formula (I):

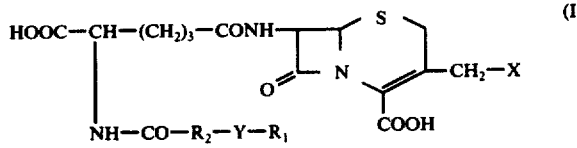

, wherein $R_1$ is a lower alkyl group, an aryl group or an aralkyl group, $R_2$ is a lower alkylene group, Y is a sulfur atom or a sulfinyl group and X is a hydrogen atom, an acetoxy group, an azido group or a group of the formula —$SR_3$ in which $R_3$ is a heterocyclic group which may be substituted by methyl group(s), and salts or adducts thereof.

It is an object of the invention to provide new cephalosporin derivatives represented by the above formula (I) and salts or adduct thereof. Another object of the invention is to provide a process for the preparation of the compounds (I). Still another object of the invention is to provide an industrially advantageous process for recovering cephalosporin C and deacetoxycephalosporin C from a fermentation broth thereof. Yet another object of the invention is to provide an industrially useful process for the preparation of 7-aminocephalosporanic acid and its derivatives at the 3rd position which are key intermediates for various important cephalosporins. Further objects and features of the invention will become apparent in the following description.

As for the methods of recovering cephalosporin C, U.S. Pat. No. 3,467,654 discloses that a fermentation broth of cephalosporin C is treated with acetone to precipitate impure materials which are filtered off, the filtrate is passed through an anion exchange resin to adsorb cephalosporin C on it and cephalosporin C is eluted with an acidic buffer. In Japanese Pat. Publication No. 61,494/1973 there also described the method for extracting cepahalosporin C which comprises by acylating cephalosporin C with a halogeno aliphatic acid and adding quinoline to the mixture at about pH 3 to precipitate quinoline salt of N-halogeno acyl-cephalosporin C. The latter method is a considerably improved one among the methods for recovering cephalosporin C from its containing solution which have been known heretofore, but it is still disadvantageous because the quinoline salt does not precipitate at a concentration of 1% or less of cephalosporin C and its recovery yield also does not so good.

Under such circumstances and taking into consideration of cephalosporin C concentration in the broths obtained by its industrial fermentation being about 0.3%, the inventors have achieved the invention as a result of various investigations on methods for recovering cephalosporin C in good yield and economically even from its solution at low concentration.

According to the invention, it provides a process for recovering cephalosporin C or its deacetoxy compound which comprises by reacting an aqueous solution containing cephalosporin C or its deacetoxy compound with a reactive derivative of an acid of the general formula (II):

$$R_1 - Y - R_2 - COOH \qquad (II)$$

, wherein all the symbols are the same as defined in the formula (I), to give an aqueous solution containing N-acyl-cephalosporin C of its deacetoxy compound of the gneral formula (III):

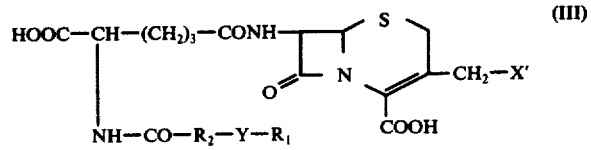

, wherein X' is an aceioxy group or a hydrogen atom and other symbols are the same as defined in the formula (I), then adding quinoline or isoquinoline to the solution and adjusting it to about pH 2.0 - 3.5 with addition of an acidifying agent and if needed, adding further an inorganic base to it.

An aqueous solution containing cephalosporin C and-/or its deacetoxy compound at their low concentration such as about 0.3% to 8% (W/V) may be used for the aqueous solution containing cephalosporin C or its deacetoxy compound in the invention. Such aqueous solution includes fermentation broths of cephalosporin C or its deacetoxy compound which are partially purified by the conventional treatment in the art such as filtration, acetone treatment and ion-exchange resin treatment and the like, or are partially concentrated. However, it is not convenient to use a solution at too high concentration of cephalosporin C, because of difficulty of recovering an adduct of N-acylcephalosporin C with an organic base which tends to become muddy. On the other hand, the use at very low concentration of cephalosporin C tends to down its recovery yield. It also is not recommended, from technical and economical viewpoints, to concentrate the fermentation broth as mentioned above, because it needs a large heat source and laborious works and further attends on undesirable decomposition of cephalosporin C. In the invention it therefor is preferred to use the fermentation broth which was subjected only to a partial purification to remove materials which may give a bad influence on acylation, e.g., monoaminomonocarboxylic acid, or was concentrated in minimum extent.

Such aqueous solution containing cephalosporin C or its deacetoxy compound is allowed to react with a reactive derivative of the acid of the formula (II).

Lower alkyl group of the symbol $R_1$ in the abovementioned formulae includes a straight or branched-chain alkyl group having one to five carbon atoms. Lower alkylene group of the symbol $R_2$ includes a straight or branched-chain alkyl group having one to three carbon atoms.

Concrete examples of the above acid are mentioned by the following chemical formulae:

| | |
|---|---|
| $CH_3S-CH_2COOH$, | $CH_3SO-CH_2COOH$ |
| $C_2H_5S-CH_2COOH$, | $C_2H_5SO-CH_2COOH$ |
| $C_6H_5S-CH_2COOH$, | $C_6H_5SO-CH_2COOH$ |

-continued

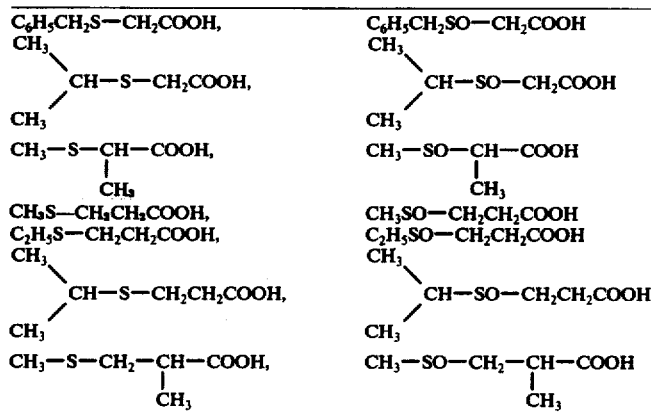

As the reactive derivatives of the acid, it is desired to use an reactive derivative being capable to acylate the amino group at the side chain of cephalosporin C and its deacetoxy compound at temperatures of about 0° to 30° C and at their low concentration. It is also desired to select the reactive derivative, taking into consideration of economy. Thus, as preferable examples of the reactive derivatives to be used in the invention there may be mentioned the mixed anhydride of the acid of the formula (II) with an aliphatic acid such as acetic acid, propionic acid, α-methylpropionic acid, butyric acid, α-ethylbutyric acid, valeric acid, pivaloic acid or 2-ethylhexanoic acid, or alkyl halocarbonate such as ethyl chlorocarbonate, butyl chlorocarbonate or isobutyl chlorocarbonate. That is, preferable examples of other acids to be used for the raw material of the mixed anhydride are ones having a dissociation constant of at least one-half and, suitably about one-fifth, of the dissociation constant of the acid of the formula (II). Besides, the acid halide or the like may be usable.

The acylation may be preferably carried out at approximately 0° - 30° C and pH 7 - 11, more preferably about pH 8 - 9.5. It is preferred to maintain a desired pH during the acylation, adding an appropriate base or with addition of an appropriate buffer agent, because of its having an tendency to lower pH value.

An use amount of the acylating agent depends upon the kind of the fermention broth to be treated. For example, in case of a broth subjected to a partial purification with an ion exhange resin, about 1.5 to 4.0 molecular amounts of the acylating agent to one molecular amount of cephalosporin C contained in it will give a good result. Also, for a broth subjected to a partial purification with acetone there will be required to use about 4 to 7 molecular amounts of the acylating agent.

The resulting N-acylcephalosporin C or its deacetoxy compound of the formula (III) is treated with quinoline or isoquinoline to precipitate from the aqueous solution. Such base may be used as single compound or in admixture thereof and is not required to be so pure. An use amount of the base is about 2 - 5 molecular amounts to one molecular amount of N-acyl-cephalosporin C.

After addition of the base, the mixture is adjusted to pH 2.0 - 3.5 with an acidifying agent such as sulfuric acid, hydrochloric acid, nitric acid, phosphoric acid or the like and stirred for about one hour at 0° - 30° C, usually 10° - 20° C to precipitate N-acyl-cephalosporin C or its deacetoxy compound with the base. This precipitate is considered to be an adduct and usually is crystalline.

Furthermore, when the resulting product is difficult to precipitate in relation to its concentration or other components in the reaction mixture, it is desired to add to the reaction mixture an inorganic salt such as sodium sulfate or sodium chloride. The the precipitate resulted may be separated by using the conventional separation procedure, e.g., centrifugation or filtration, washed with water and then with an organic solvent such as ethyl acetate and then dried.

Thus obtained adduct of N-acyl-cephalosporin C or its deacetoxy compound and the organic base may be converted into the corresponding other derivatives at the 3rd position as well as 7-aminocephalosporanic acid or its derivatives at 3rd position. Also, the adduct may be treated with an appropriate acid to obtain free N-acyl-cephalosporin C or its deacetoxy compound which is further converted into the corresponding salt such as the alkali metal salt or trialkyl amine salt.

The derivatives at the 3rd position of N-acyl-cephalosporin C can be obtained by reacting N-acyl-cephalosporin C or adduct or salt thereof with an alkali metal azide or a thiol of the general formula (IV): HS-$R_3$ wherein $R_3$ is the same meaning as defined above, or salt thereof.

The reaction may be conducted in an aqueous solvent, adjusting to pH 5.0 - 8.0. The aqueous solvent to be used includes water itself or a mixture of water and an organic solvent such as a lower aliphatic alcohol (e.g., methanol), acetone, dioxane or the like. It is desired to select a suitable solvent taking into consideration of solubility of reagents in water. It is convenient to add to te reaction mixture, for example, a phosphate buffer in order to control pH value during the reaction. It also is generally desired to heat the reaction system.

Preferred examples of the thiol of the formula (IV) include thiadiazole-thiol such as 1,3,4-thiadiazole-2-thiol or 5-methyl-1,3,4-thiadiazole-2-thiol; tetrazole-thiol such as tetrazole-5-thiol or 1-methyltetrazole-5-thiol; oxadiazole-thiol such as 1,3,4-oxadiazole-2-thiol or 5-methyl-1,3,4-oxadiazole-2-thiol, and like compounds.

The resulting 3-substituted compound may be isolated by making aqueous reaction mixture to an acidic pH and extracting with an organic solvent such as ethyl acetate. When desired, a purification such as one using charcoal may be conducted during the above procedure. Furthermore, the organic extract as it is may be used for the next reaction for removal of the acyl group at the 7th position. However, when water or proton-active organic solvents exist, they should be removed before the next reaction as explained below.

Thus obtained cephalosporin derivatives of the formula (I) or adducts or salts thereof may be removed their acyl group at the 7th position to give 7-aminocephalosporanic acid and its 3-substituted derivatives.

That is, 7-aminocephalosporanic acid or its 3-substituted derivatives may be obtained by converting the cephalosporin derivative of the formula (I) or adduct or salt thereof into its protected form at the carboxy groups of the 4th and 5th positions as the early hydrolyzable ester or mixed anhydride, reacting the resultant with an iminohalide forming agent and then with an imino-ether forming agent to give the corresponding imino-ether compound and then hydrolyzing it.

As reagents to be used for protection of the carboxy groups of the cephalosporin derivative (I) there may be mentioned a phosphine-halogen compound of the general formula (V):

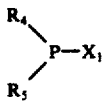

wherein $X_1$ is a halogen atom, $R_4$ is a lower alkyl or alkoxy group or a halogen atom and $R_5$ is a halogen atom or a lower alkoxy group, but when both of $R_4$ and $R_5$ are lower alkoxy groups, they may form a ring together with P atom, or a silicone-halogen compound of the general formula (VI):

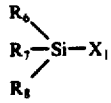

, wherein $X_1$ is a halogen atom, $R_6$ is a lower alkyl or alkoxy group or a halogen atom and $R_7$ and $R_8$ are a lower alkyl or alkoxy group.

Preferable examples of these phosphine or silicone-halogen compounds include

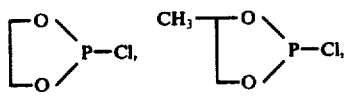

$CH_3OPCl_2$, $C_2H_5OPCl_2$, $C_4H_9OPCl_2$, $CH_3PCl_2$, $C_4H_9PCl_2$, $PCl_3$, $ClCH_2CH_2OPCl_2$, $(CH_3)_3SiCl$, $CH_3(CH_3O)_2SiCl$, $(CH_3O)_3SiCl$, $CH_3O(CH_3)_2SiCl$, $(CH_3)_2SiCl_2$, $(CH_3O)_2SiCl_2$, $CH_3(CH_3O)SiCl_2$.

More preferable examples include

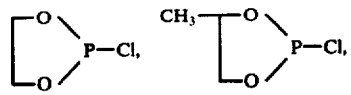

$(CH_3)_3SiCl$, $CH_3(CH_3O)_2SiCl$, $CH_3O(CH_3)_2SiCl$, $(CH_3O)_3SiCl$. Besides, $COCl_2$, $CH_3COCl$ and like compounds which are carbon-halogen compound may be used. In brief, the protection of the carboxy groups in the invention is conducted in order to make the carboxy groups inert in the following imino-halide formation and imino-ether formation and therefor the kind of the protecting group is not particularly limited. It however is desired to select a suitable reagent among the above-mentioned examples, taking into considerations of easiness of hydrolysis, cost of reagents, easiness of treatment and the like.

The reaction to convert the carboxy groups into its protected form may be conducted under anhydrous condition in an inert organic solvent such as methylene chloride, ethylene chloride, tetrahydrofuran or chloroform and in addition of an organic base such as triethylamine, N-methylmorpholine, N-methylpiperidine, quinoline, pyridine, dimethylaniline or anologue thereof.

Then the above reaction product may be reacted with an imino-halide forming agent such as phosphorus pentachloride, phosphorus oxychloride or phosgen to convert the amide bond at the 7th and 5'th positions of the cephalosporin derivated from the compound of the formula (I), into the imino-halide. To the reaction mixture is then added a lower alcohol such as methanol, propanol, butanol, amyl alcohol, ethylene glycol, propyrene glycol, ethylenechlorohydrin, alkoxyethanol or the like, to convert into the corresponding imino-ether.

Besides, the reaction mixture subjected to the protection of the carboxy groups as it is may be used in the above two reactions.

The resulting imino-ether compound as above is subjected to a hydrolysis with water to convert into the desired 7-aminocephalosporanic acid and its 3-substituted compounds.

The hydrolysis may be conducted at an acidic condition, preferably at pH below 3. Furthermore, when N-acyldeacetoxy cephalosporin C is used, it may be conducted even at pH 1.

The reaction mixture after the hydrolysis is adjusted to an isoelectric point of the resultant 7-amino compound by which the desired compound may be obtained as precipitate. The obtained precipitate is separated and dried in accordance with the conventional method.

The desired compounds according to the method of the invention may be obtained in a very high yield and purity.

The following examples are included merely to aid in the understanding of the invention, and variations may be made by one skilled in the art without departing from the spirit and scope of the invention.

EXAMPLE 1.

To 20 ml of an elution from resin containing 30 mg/ml of cephalosporin C were added about 0.2 g of sodium borate, which was adjusted to pH 9.0 with a dilute sodium hydroxide solution. To this solution were added 5 ml of a solution of the mixed anhydride in ethyl acetate (contains 2.5 moles to one mole of cephalosporin C) which was prepared from pivaloyl chloride and N-methylmorpholine salt of methylthioacetic acid and stirred vigorously at 0° – 10° C for about an hour adjusting to pH 9 with a dilute sodium hydroxide. After monitoring the completion of the reaction by Thinlayer chromatography (benzene : acetic acid : pyridine : water = 15 : 3 : 10 : 12, sprayed by a solution of iodo azide as a coloring agent and heated), the reaction mixture was adjusted to pH 5 – 6 with a dilute sulfuric acid.

An oranic layer was removed and an aqueous layer was diluted with water to make 30 ml (a solution corresponding to 2% cephalosporin C solution). To 15 ml of the aqueous solution were added 0.43 ml of quinoline (5 moles to 1 mole of cephalosporin C) and adjusted to pH 3.0 with a dilute sulfuric acid, while stirring. Crystals will soon appear. After stirring for an hour, precipitated crystals were collected, washed with a small amount of ice-water and then with ethyl acetate and dried overnight in a vacuum desiccator. Thus quinoline adduct of N-methylthioacetyl-cephalosporin C was obtained. Yield : 450 mg (97% purity by UV assay), 98%.

IR 1790 cm$^{-1}$ ($\beta$-lactam), UV $\lambda$ max 264 m$\mu$.

EXAMPLE 2.

Each of 15 ml of the reaction mixture (2% solution calculated as cephalosporin C) obtained from 3% cephalosporin C solution in accordance with Example 1 was diluted as follows and to each were added 0.43 ml of quinoline (5 moles to one mole of cephalosporin C), followed to the treatment according to Example 1.

Yields of quinoline adduct of N-methylthioacetyl-cephalosporin C were as follows. (FIGS. in parenthesis show yields when diluted with 5% sodium chloride solution)

|    |                     | Yield              |              |
|----|---------------------|--------------------|--------------|
| a) | 1 % solution, 30 ml | 426mg, (441mg),    | 93% (96%)    |
| b) | 0.5 % solution, 60 ml | 415mg, (436mg),  | 90% (94%)    |
| c) | 0.3 % solution, 100 ml | 380mg, (403mg), | 83% (87%)    |

EXAMPLE 3.

To 20 ml of an elution from resin containing 15 mg/ml (by UV assay) of cephalosporin C were added about 0.2 g of sodium hydrogen phosphate and adjusted to pH 9.0 with a dilute sodium hydroxide solution. To this mixture were added 5 ml of a solution of the mixed anhydride* in ethyl acetate prepared from potassium methylthioacetate, propionyl chloride and a slight amount of N-methylmorpholine (*contains 2.5 moles to one mole of cephalosporin C) and stirred vigorously at 0 - 10° C for about an hour, maintaining pH 9 with a dilute sodium hydroxide solution. The reaction mixture was adjusted to pH 5 - 6. After separating out an organic layer, an aqueous layer was diluted with 5% sodium chloride solution to make 30 ml (corresponds to 1% solution calculated as cephalosporin C).

To 15 ml of the solution were added 0.22 ml of isoquinoline (5 moles to one moe of cephalosporin C) and adjusted to pH 3.0 with a dilute sulfuric acid at 10° C with stirring. Very soon crystals are separated out. After stirring for an hour, the crystals were collected and washed with a small amount of ice-water, then with ethyl acetate and dried overnight in a vacuum desiccator, by which 228 mg (Yield : 97%) of isoquinoline adduct of N-methylthioacetylcephalosporin C, purity of 97% (by UV assay) were obtained. UV $\lambda$ max 263 m$\mu$.

15 ml of the remaining reaction solution were diluted with 5% sodium chloride solution to make 30 ml (corresponds to 0.5% solution calculated as cephalosporin C). After adding 0.22 ml of quinoline to the solution, the mixture was adjusted to pH 3.0 and stirred at 5 - 10° C. Very soon crystals are separated out. The crystals were collected after an hour, washed with ice-water and with ethyl acetate and dried in vacuo. 226 mg of isoquinoline adduct of N-methylthioacetyl-cephalosporin C having 97% purity were obtained.

EXAMPLE 4.

To 10 ml of an elution from resin which was controlled to contain 10 mg/ml of cephalosporin C, were added about 0.04 g of sodium borate and adjusted to pH 9.0 with a dilute sodium hydroxide solution. To this mixture were added 3 ml of a solution of the mixed anhydride (contains 2.5 moles to one mole of cephalosporin C) in ethyl acetate prepared from potassium methylthioacetate, a slight amount of N-methylmorpholine and acetyl chloride. The mixture was vigorously stirred at 10° - 20° C for about an hour, maintaining pH 9.0 with a dilute sodium hydroxide solution.

To the reaction mixture were added 0.1 ml of quinoline and then 10% phosphoric acid solution to adjust to pH 3.0 with stirring. Very soon crystals are separated out. After stirring for about an hour, the crystals were collected and washed with a small amount of ice-water, then with ethyl acetate and dried overnight in a vacuum desiccator, by which 145 mg of quinoline adduct of N-methylthioacetyl-cephalosporin C (98% purity) were obtained.

IR and UV spectrum of the product coincided in those of the authenic sample.

When N-acetylation was carried out in use of acetic anhydride instead of the above-mentioned acid anhydride, the desired crystals of quinoline adduct could not be obtained.

EXAMPLE 5.

Quinoline adduct of N-methylthioacetyl-cephalosporin C, 150 mg (98% purity) was obtained by the treatment in accordance with Example 4, but an ethyl acetate solution of the acid anhydride prepared from methylthioacetyl chloride and N-methylmorpholine salt of methylthioacetic acid was used instead of the solution of the mixed anhydride of methylthioacetic acid and acetic acid.

EXAMPLE 6.

Quinoline adduct of N-ethylthioacetyl-cephalosporin C, 125 mg (96% purity) was obtained by the treatment in accordance with Example 4, but an ethylthioacetate solution of the mixed anhydride prepared from potassium ethylthioacetate, propionyl chloride and a slight amount of N-methylmorepholine was used instead of the mixed anhydride of methylthioacetic acid and acetic acid in Example 4.

IR 1790 cm$^{-1}$, UV $\lambda$ max 263 m$\mu$.

EXAMPLE 7.

Instead of the mixed anhydride of methylthioacetic acid and acetic acid in Example 4, each ethyl acetate solutions of (a) the mixed anhydride prepared from potassium isopropylthioacetate, pivaloyl chloride and a slight amount of N-methylmorpholine, (b) the mixed anhydride from potassium isobutylthioacetate, pivaloyl chloride and a slight amount of N-methylmorpholine, (c) the mixed anhydride from potassium $\alpha$-methylthiopropionate, propionyl chloride and a slight amount of N-methylmorpholine and (d) the mixed anhydride from potassium methylsulfinylacetate, pivaloyl chloride and a slight amount of N-methylmorpholine was treated in accordance with Example 4, the results of which were as follows:
a. Quinoline adduct of N-isopropylthioacetyl-cephalosporin C, 108 mg (95% purity), UV λ max 263 mμ.
b. Quinoline adduct of N-isobutylthioacetyl-cephalosporin C, 105 mg (96% purity), UV λ max 263 mμ.
c. Quinoline adduct of N-α-methylthiopropionyl-cephalosporin C, 134 mg (97% purity), UV λ max 263 mμ.
d. Quinoline adduct of N-methylsulfinylacetyl-cephalosporin C, 138 mg (94% purity), UV λ max 263 mμ.

EXAMPLE 8.

Instead of the mixed anhydride of methylthioacetic acid and acetic acid in Example 4, each ethyl acetate solutions of (a) the mixed anhydride prepared from potassium β-methylthiopropionate, pivaloyl chloride and a slight amount of N-methylmorpholine, and (b) the mixed anhydride from potassium β-ethylthiopropionate, pivaloyl chloride and a slight amount of N-methylmorpholine was used and treated in accordance with Example 4, the results of which are as follows:
a. Quinoline adduct of N-β-methylthiopropionyl-cephalosporin C, 100 mg (96& purity), IR 1790 cm$^{-1}$, UV λ max 263 mμ.
b. Quinoline adduct of N-β-ethylthiopropionyl-cephalosporin C, 82 mg (96% purity), IR 1790 cm$^{-1}$, UV λ max 263 mμ.

EXAMPLE 9.

0.63 of dried quinoline adduct of N-methylthioacetyl-cephalosporin C, 0.3 g of triethylamine and 0.4 g of dimethylaniline were added to 10 ml of dried methylene chloride and to the mixture was dropwise added a solution of 0.43 g of trimethylsilyl chloride in methylene chloride at 0° C with stirring. After about 30 mins., to the resulting clear solution cooled at −30° C were added 0.5 g of a fine powder of phosphorus pentachloride and stirred for 2 hrs. at −20 − −5° C. Then the mixture was again cooled to −30° C. 3 ml of anhydrous isobutanol were added dropwise to the cooled mixture, stirred for 2 hrs. at −30° − −10° C and kept for overnight at −20° C. 3 ml of ice-water were then added to this mixture and stirred for 30 mins., maintaining pH 2.0 − 2.5 with ammonium carbonate. Then the mixture was gradually adjusted to pH 3.5 of isoelectric point and kept for overnight in an ice-box. The precipitated crystals were collected by centrifugation, washed with a small amount of cooled 60% acetone-water and then with acetone and dried.

7-Aminocephalosporanic acid, 0.23 g (Yield : 84%, Purity : 98% by UV assay) was obtained.
IR 1800 cm$^{-1}$, UV λ max 262 mμ.

EXAMPLE 10.

Instead of trimethylsilyl chloride in Example 9, (a) 2-chloro-1,3,2-dioxaphospholane 0.5 g, (b) 2-chloro-4-methyl -1,3,2-dioxaphospholane 0.55 g, (c) trimethoxysilyl chloride 0.63 g and (d) dimethyl-methoxysilyl chloride 0.5 g were used and treated in a similar way to Example 9 respectively. 7-Aminocephalosporanic acid was obtained by the respective yield of (a) 0.22 g, (b) 0.24 g, (c) 0.23 g and (d) 0.23 g.

EXAMPLE 11.

Instead of isobutyl alcohol in Example 9, (a) anhydrous methanol and (b) n-butanol were used and treated in a similar way to Example 9, respectively. 7-Aminocephalosporic acid was obtained by the respective yield of (a) 0.25 g and (b) 0.21 g.

EXAMPLE 12.

To 20 ml of "an elution from resin" adjusted to contain 10 mg/ml of cephalosporin C were added about 0.08 g of sodium borate and adjusted to pH 9.0 with a dilute sodium hydroxide solution. To this solution were added 5 ml of a solution of the mixed anhydride in ethyl acetate (contains 4 moles to one mole of cephalosporin C) which was prepared from potassium methylthioacetate, a slight amount of N-methylmorpholine and ethyl chlorocarbonate and stirred vigorously at 0° − 5° C. The mixture was allowed to react for about an hour, maintaining pH 9 with a dilute sodium hydroxide solution. To the reaction mixture were added 0.2 ml of quinoline and the resultant was under stirring adjusted to pH 3.0. The mixture was then saturated with sodium chloride, stirred for about an hour, filtered to collect crystals which were washed with ice-water and ethyl acetate and then dried. Thus quinoline adductof N-methyl-thioacetyl-cephalosporin C, 260 mg (97% purity) was obtained.

EXAMPLE 13.

a. Quinoline adduct of 5'-methylthioacetyl-cephalosporin C, 3.8 g was suspended in 25 ml of water, adjusted to pH 6.5 with 2N-aqueous sodium hydroxide solution and washed several times with methylene chloride. Then to the mixture were added 0.8 g of 1-methyltetrazole-5-thiol and 0.5 g of sodium hydrogen phosphate and adjusted again to pH 6.5 with sodium hydroxide. The mixture was stirred for 5 − 8 hrs. at 60° − 70° C. (The reaction mixture was monitored by Thin-layer chromatography.) After completing the reaction, the mixture was adjusted to pH 2.0 with a dilute sulfuric acid, extracted several times with ethyl acetate, washed four times with a small amount of an aqueous saturated sodium chloride solution, dried over magnesium sulfate and then distilled in vacuo to remove the solvent. The residue was treated with n-hexane to solidify, by which 2.3 g of 7-(5'-N-methylthioacetamido)-adipoamido) -3-(1''-methyltetrazol-5''-yl)-thiomethyl-3-cephem-4-carboxylic acid (Yield : 84%) were obtained.
IR (KBr) 1770 cm$^{-1}$, UV λ max 272 mμ.

b. The compound (1.1 g) obtained in the above a) was dried over phosphorus pentaoxide at 70° − 80° C in vacuo. Dry methylene chloride (10 ml), dimethylaniline (2.4 g) and methyldichlorophosphite (1.3 g) were added to the above dried compound and stirred at room temperature. After 30 mins., the clear solution was cooled to −30° C. To this mixture were added, with stirring, 1.2 g of phosphorus pentachloride which was allowed to react for 2 hours at −20 − 0° C and then cooled to −40° C again. 2.6 g of anhydrous methanol were dropwise added to the reaction mixture, stirred for 2 hours at −20° C − −5° C and stand overnight at −20° C. The mixture was put into 7 ml of ice-water, stirred for 20 mins., and then gradually adjusted to pH 3.5 with ammonium carbonate. Then the mixture was kept for overnight, and adjusted to pH 3.5 again and the crystals were collected by centrifugation. The crystals were washed with cold 60% aqueous acetone, centrifuged and again washed with acetone. 0.55 g (Yield : 86%) of 7-amino-3-(1'-methyltetrazol-5'-yl)-thiomethyl-3-cephem-4-carboxylic acid were obtained.

IR : 1800 cm⁻¹, UV λ max : 272 mμ.

c. The experiment was repeated in the same reagents and treatment as above but trimethoxysilylchloride 3.1 g was used instead of methyldichlorophosphite. Its yield was 80%.

d. The experiment was repeated in the same reagents and treatment as above, but acetyl chloride 1.6 g and ethylene glycol 3.7 g were used instead of methyldichlorophosphite and methanol respectively. Its yield was 73%.

EXAMPLE 14.

a. 5-Methyl-1,3,4-thiadiazole-2-thiol instead of 1-methyltetrazole-5-thiol was used and treated in the same way as in a. of Example 13, by which 2.4 g (Yield : 84%) of 7-[(5'-methylthioacetamido)-adipoamido]-3-(5''-methyl-1'', 3'', 4'' -thiaziazol-2''-yl)-thiomethyl-3-cephem-4-carboxylic acid were obtained.

IR : 1780 cm⁻¹, UV λ max : 272 mμ.

b. The product 1.2 g obtained in above a. was treated in the same way as in b. of Example 13, by which 0.6 g (Yield : 87%) of 7-amino-3-(5'-methyl-1',3',4'-thiadiazol-2'-yl) -thiomethyl-3-cephem-4-carboxylic acid were obtained.

IR : 1800 cm⁻¹, UV λ max : 272 mμ.

EXAMPLE 15.

a. 1,3,4-Thiadiazole-2-thiol instead of 1-methyltetrazole-5-thiol in a. of Example 13 was used and treated in the same way as in a. of Example 13, by which 2.3 g (Yield : 82%) of 7-[(5'-N-methylthioacetamido)-adipoamido]-3-(1',3',4'-thiaziazol-2'-yl)-thiomethyl-3-cephem-4-carboxylic acid were obtained.

IR : 1780 cm⁻¹, UV λ max : 270 mμ.

b. The product 1.1 g obtained by the above a. was used and treated in the same way as in b. of Example 13, by which 0.5 g (Yield : 83%) of 7-amino-3-(1',3',4'-thiadiazol-2'-yl)-thiomethyl-3-cephem-4-carboxylic acid were obtained.

IR : 1800 cm⁻¹, UV λ max : 270 mμ.

I claim:

1. A compound of the formula

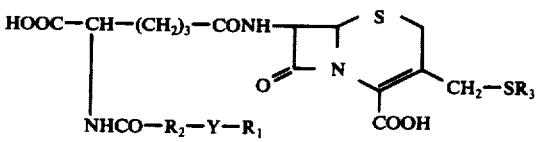

wherein
R₁ is a lower alkyl, phenyl or benzyl group, R₂ is a lower alkylene group, Y is a sulfur atom or a sulfinyl group and R₃ is a thiadiazolyl, tetrazolyl or oxadiazolyl group;
or a pharmaceutically acceptable salt or adduct thereof.

2. The compound of claim 1, wherein R₃ is substituted by a methyl group.

3. 7-[(5'-N-Methylthioacetamido)-adipoamido]-3-(1''-methyltetrazol-5''-yl)-thiomethyl-3-cephem-4-carboxylic acid in accordance with claim 1.

4. 7-[(5-N-Methylthioacetamido)-adipoamido]-3-(5''-methyl-1'',3'',4''-thiadiazol-2''-yl)-thiomethyl-3-cephem-4-carboxylic acid in accordance with claim 1.

5. 7-[(5'-N-Methylthioacetamido)-adipoamido]-3-(1',3', 4'-thiadiazol-2'-yl)-thiomethyl-3-cephem-4-carboxylic acid in accordance with claim 1.

* * * * *